United States Patent [19]

Freedman, Jr. et al.

[11] Patent Number: 5,755,756
[45] Date of Patent: May 26, 1998

[54] HYPOTHERMIA-INDUCING RESUSCITATION UNIT

[76] Inventors: Robert J. Freedman, Jr., 711 Kimball Ave.; Gary P. Jones, 3214 Carroll Ct., both of Alexandria, La. 71301

[21] Appl. No.: 529,221

[22] Filed: Sep. 15, 1995

[51] Int. Cl.$^6$ .......................... A47C 21/00; A61F 7/00; A61F 7/12
[52] U.S. Cl. ........................ 607/110; 607/105; 607/96
[58] Field of Search ...................... 607/96, 104, 105–114; 128/747, 845; 600/16–18, 21; 5/625–629, 421–423

[56] References Cited

U.S. PATENT DOCUMENTS

| | | |
|---|---|---|
| 2,702,552 | 2/1955 | Moodie . |
| 3,125,096 | 3/1964 | Antiles et al. ............... 607/105 |
| 3,477,424 | 11/1969 | Tracy . |
| 4,060,079 | 11/1977 | Reinhold, Jr. ............... 600/21 |
| 4,300,547 | 11/1981 | Pasternack . |
| 4,353,359 | 10/1982 | Milbauer . |
| 4,586,500 | 5/1986 | Glynn . |
| 4,738,119 | 4/1988 | Zafred . |
| 4,765,338 | 8/1988 | Turner et al. . |
| 4,858,259 | 8/1989 | Simmons et al. . |
| 4,865,012 | 9/1989 | Kelley . |
| 4,920,963 | 5/1990 | Brader . |
| 5,063,924 | 11/1991 | Galvan et al. . |
| 5,107,857 | 4/1992 | Linnemann et al. ............... 128/845 |
| 5,146,625 | 9/1992 | Steele et al. . |
| 5,172,689 | 12/1992 | Wright . |
| 5,257,429 | 11/1993 | Genis . |
| 5,261,399 | 11/1993 | Klatz et al. . |
| 5,292,347 | 3/1994 | Pompei . |
| 5,295,949 | 3/1994 | Hathaway . |
| 5,305,471 | 4/1994 | Steele et al. . |
| 5,402,542 | 4/1995 | Viard ............... 5/421 |
| 5,486,204 | 1/1996 | Clifton ............... 607/96 |

OTHER PUBLICATIONS

Zhen-sheng Zbeng, et al., "Sequential External Counterpulsation (SECP) in China," 1983, pp. 1–5.

Zhen-sheng Zheng, et al., "New Sequential External Counterpulsation for the Treatment of Acute Myocardial Infarction," Aug. 1984, pp. 470–476.

W.E. Lawson, et al., "Efficacy of Enhanced External Counterpulsation in the Treatment of Angina Pectoris," 1992, p. 1.

William E. Lawson, M.D., et al., "Efficacy of Enhanced External Counterpulsation in the Treatment of Angina Pectoris," Oct. 1, 1992, pp. 859–862.

Zvi Oster, M.D., "Guidelines for the Submission of Abstracts," Apr. 30, 1993, p. 1.

(List continued on next page.)

Primary Examiner—Jennifer Bahr
Assistant Examiner—Samuel Gilbert
Attorney, Agent, or Firm—Senniger, Powers, Leavitt & Roedel

[57] ABSTRACT

An apparatus of the present invention induces hypothermia in a patient and effects cardio-pulmonary resuscitation on the patient. The apparatus including a gurney for supporting and facilitating transport of the patient, the gurney having at least a portion thereof in fluid communication with a coolant source, and a body suit having a thoracic cuff and an abdominal cuff. The thoracic and abdominal cuffs are sequentially inflatable and deflatable for sequentially compressing and releasing the thoracic and abdominal region of the patient to induce inhalation and exhalation in the lungs and circulation of the blood supply in the patient. The apparatus further including a head cooling device which includes a helmet adapted to be mounted on the head of the patient and a mask in fluid communication with a cooled oxygen source for supplying cooled oxygen to the lungs of the patient. The helmet of the head cooling device having an outer shell and a bladder mounted on the outer shell in fluid communication with the coolant source for extracranial cooling of the brain.

34 Claims, 4 Drawing Sheets

OTHER PUBLICATIONS

Author unknown, "Enhanced External Counterpulsation (EECP)," date unknown, p. 130.

Future Medical Products, Inc., "Enhanced External Counterpulsation (EECP) Fact Sheet," Mar. 1994, pp. 1–3.

William E. Lawson, et al., "Benefits are Sustained at 3–Year Follow–up in Patients Who Have Been Treated With Enhanced External Counterpulsation," Mar. 13, 1994, p. 1.

Laura Gordon, "Blood–pump Cuffs Curb Angina," Apr. 21, 1994, p. 1.

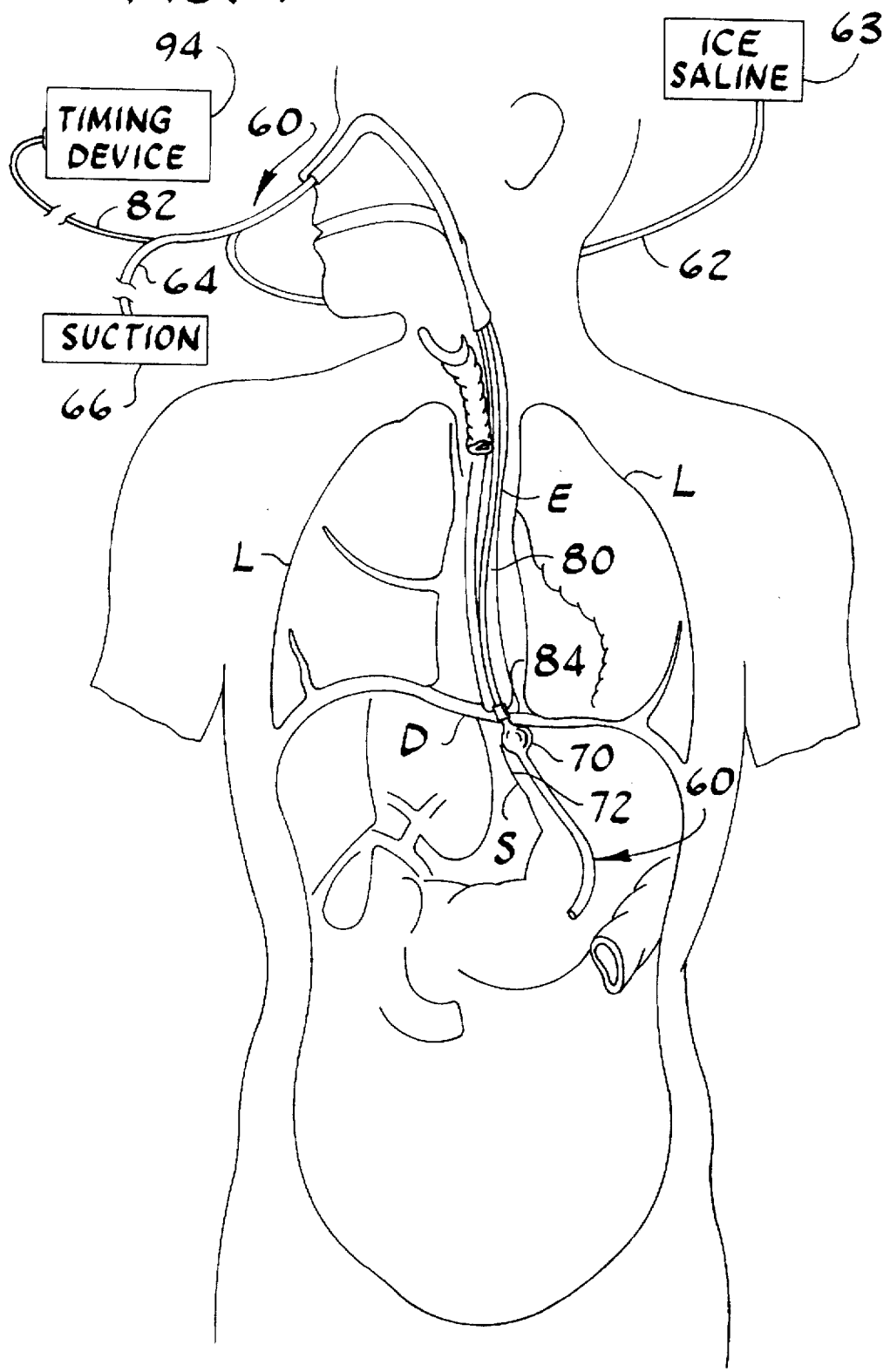

HYPOTHERMIA-INDUCING RESUSCITATION UNIT

BACKGROUND OF THE INVENTION

The present invention relates to an apparatus for providing circulatory and pulmonary support while inhibiting tissue metabolism in the brain and more particularly a method and apparatus for inducing hypothermia while effecting cardio-pulmonary resuscitation during emergency treatment of cardiac arrest.

It is well-known that hypothermia can dramatically postpone the neurologic deterioration in hypoxic or anoxic tissue. For example, accidental submersion in cold waters resulting in hypothermia has consistently contributed to the neurologic survival of the accident victims who otherwise would have sustained irreparable brain damage. Observation of this phenomenon has led medical practitioners to intentionally induce hypothermia in the course of various hypoxia and anoxia-producing surgical procedures in order to increase both the systemic metabolism and the associated overall oxygen requirements. This intentional inducement of hypothermia is easily accomplished in a hospital setting. For instance, during a surgical procedure, heat is removed from the body by cooling the blood as it is extracted from the body through a pump. As it is recirculated in the body, the core of the body and brain is cooled. Emergency inducement of hypothermia in a non-hospital setting, however, is much more demanding. As a result, induced hypothermia forms no part of pre-hospital emergency cardiac care.

Prior designs for inducing hypothermia in a non-hospital environment, such as the apparatus disclosed in U.S. Pat. Nos. 4,920,963 and 5,362,399, relate to extracranial, non-invasive methods of cooling the head of the victim. Although such designs may ultimately induce hypothermia, the procedure is time-consuming. The benefits associated with inducing hypothermia are only realized if the hypothermia is quickly induced (i.e., before the onset of brain damage).

SUMMARY OF THE INVENTION

Among the several objects and features of the present invention may be noted the provision of an apparatus which rapidly induces hypothermia; the provisions of such an apparatus which incorporates non-invasive, external cooling with invasive, internal cooling; the provisions of such an apparatus which effects cardio-pulmonary resuscitation; and the provision of such an apparatus which is portable.

Generally, an apparatus of the present invention induces hypothermia in a patient while it effects cardio-pulmonary resuscitation on the patient. The apparatus comprises a gurney for supporting and facilitating transport of the patient, the gurney having at least a portion thereof in fluid communication with a coolant source, and a body suit having a thoracic cuff and an abdominal cuff. The thoracic and abdominal cuffs are sequentially inflatable and deflatable for sequentially compressing and releasing the thoracic and abdominal region of the patient to induce inhalation and exhalation in the lungs and circulation of the blood supply in the patient. The apparatus further includes a head cooling device which includes a helmet adapted to be mounted on the head of the patient and a mask in fluid communication with a cooled oxygen source for supplying cooled oxygen to the lungs of the patient. The helmet of the head cooling device comprises an outer shell and a bladder mounted on the outer shell in fluid communication with the coolant source for extracranial cooling of the brain.

Other objects and features will be in part apparent and in part pointed out hereinafter.

BRIEF DESCRIPTION OF THE DRAWINGS

FIG. 4 is a side elevational view of the mask with the nasogastric tube shown inside the patient.

Corresponding reference characters indicate corresponding parts throughout the several views of the drawings.

DETAILED DESCRIPTION OF THE PREFERRED EMBODIMENT

Figure 1:
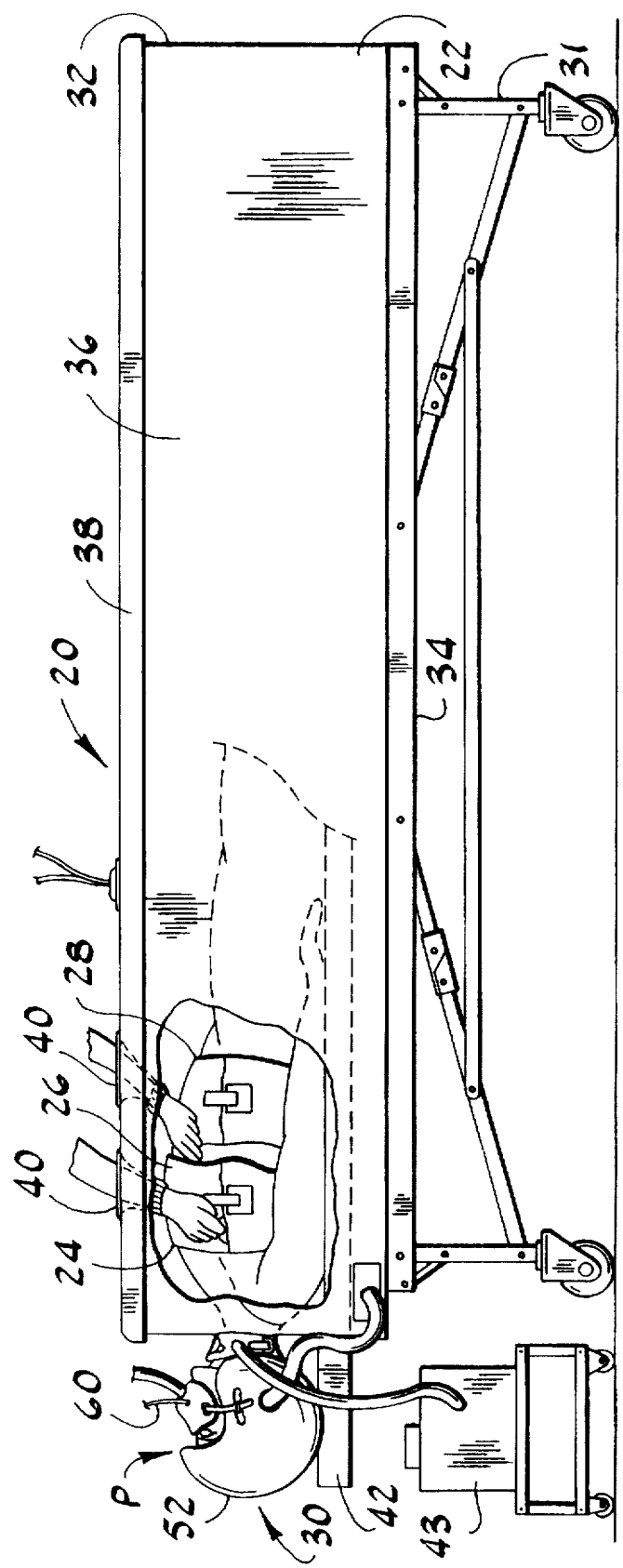
FIG. 1 is a elevational view of the apparatus of the present invention showing a patient lying on the gurney with the thoracic and abdominal cuffs situated on the patient and the head cooling device located on the patient.
Figure 2:
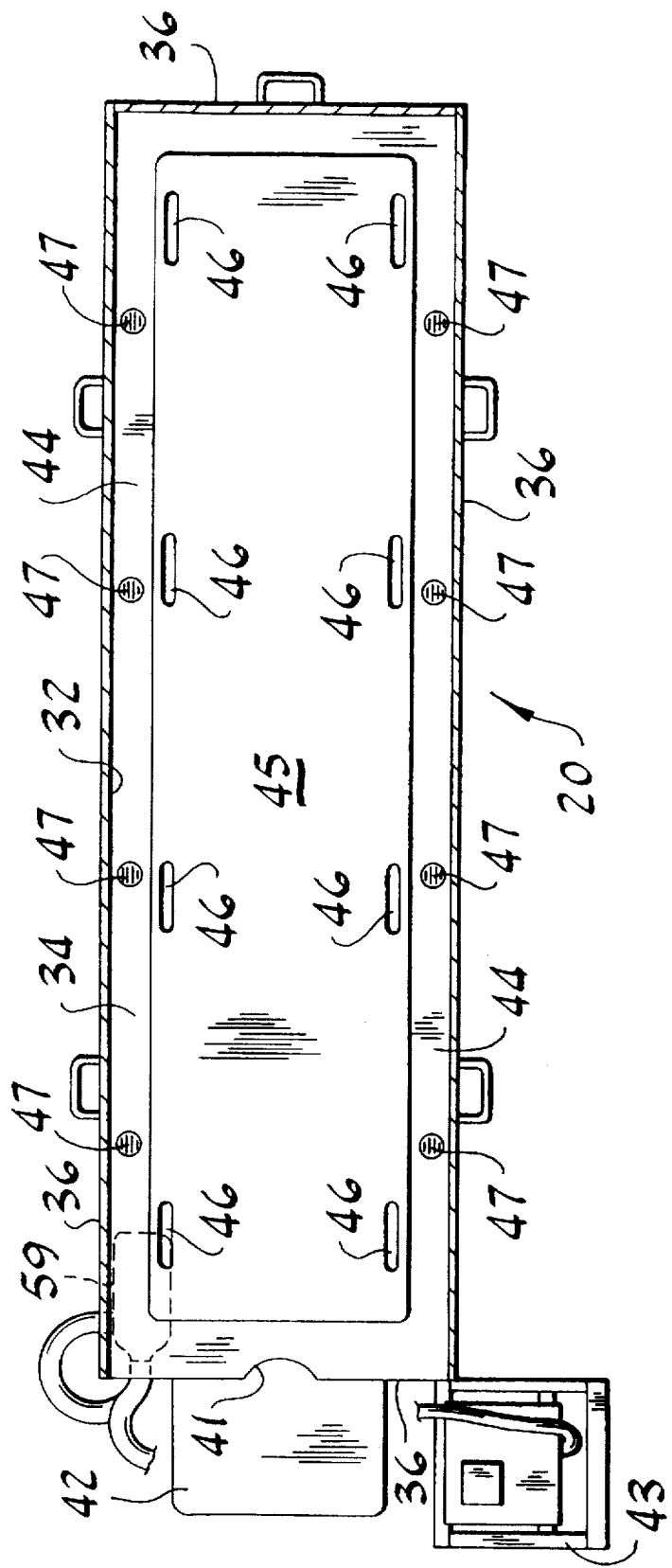
FIG. 2 is a top plan view of the gurney.
Figure 3:
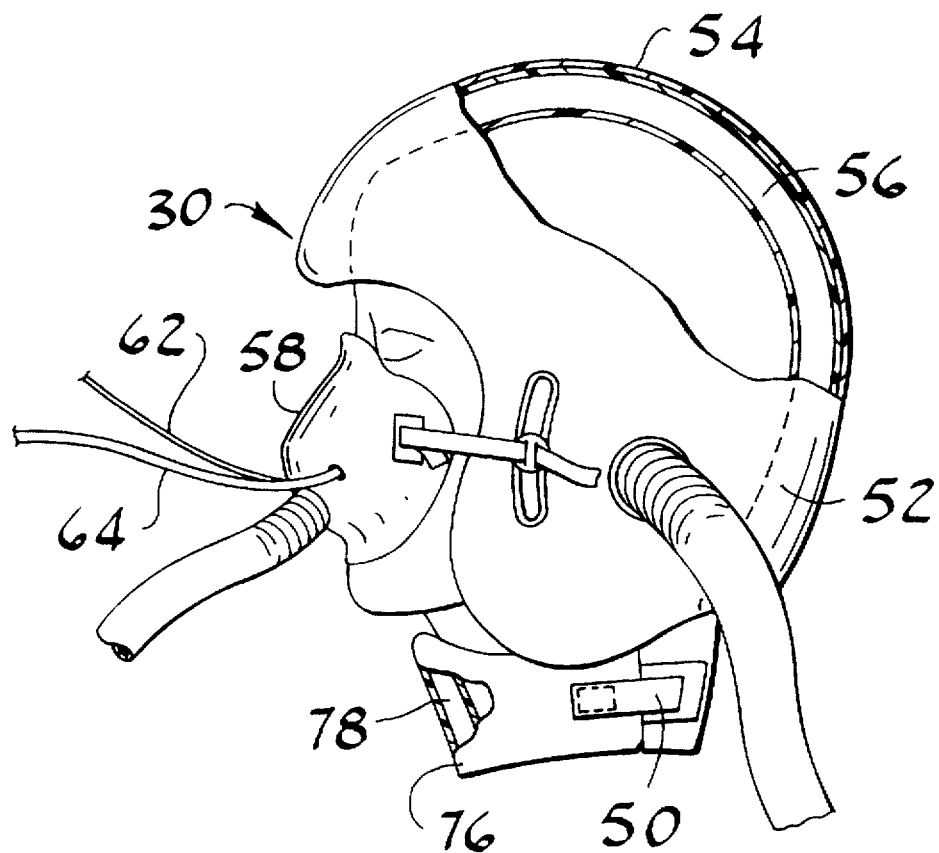
FIG. 3 is a cross-sectional view of the helmet of the head cooling device of the present invention.
Figure 5:
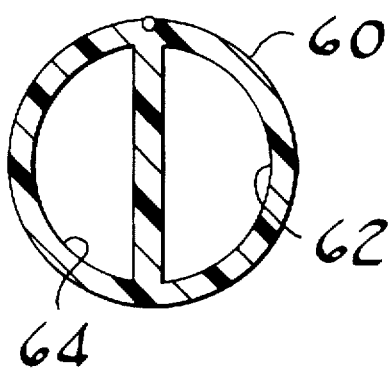
FIG. 5 is a cross-sectional view of the nasogastric tube.

Referring now to the drawings, an apparatus for inducing hypothermia in a patient P and effecting cardio-pulmonary resuscitation on the patient is indicated generally at 20. The apparatus comprises a gurney 22 for supporting a patient and facilitating the patient's transport, a body suit 24 having a thoracic cuff 26, an abdominal cuff 28 and lower-torso cuffs (not shown) to induce inhalation and exhalation in the lungs and effect circulation of the blood supply, and a head cooling device 30 for extracranial cooling of the brain and supplying cooled oxygen to the lungs of the patient.

The gurney 22 is designed to support the patient in a proper position so that emergency treatment may be performed and to facilitate the transport of the patient. As is typical, the gurney 22 includes a collapsible, wheeled base 31 for quick transport of the patient from the emergency site into the ambulance. The gurney 22 also includes a refrigerated compartment 32 in which the patient is placed. The compartment 32 has a bottom surface 34 on which the patient lies, side walls 36 and a removable lid 38. In order to permit emergency care to be performed on the patient, the lid preferably includes portals 40 in order for the hands and arms of emergency-care providers to be inserted into the compartment 32 and on the patient. The gurney 22 further includes a headrest 42 adjacent the compartment 32 for supporting the patient's head. This headrest 42 is positioned outside of the compartment to enable the head cooling device 30 to be positioned thereon. The side wall of the compartment adjacent the headrest 42 includes an opening 41 to receive the neck of the patient.

This compartment 32 is cooled by the introduction of a coolant source as the patient is lying therein. The coolant source is preferably a compressed liquid (or gas) such as carbon dioxide, which upon decompression becomes a cold gas. Prior to introduction into the compartment (or other activation), these cold compressed liquids are preferably stored in portable containers such as a tank 43 that is carried on the gurney 22. To introduce the coolant in the compartment, passageways 44 extend longitudinally along each side of the compartment from one end of the gurney to the other end. These passageways 44 are in fluid communication with the $CO_2$ tank 43 and include vents 47 for circulating the coolant over the patient as the patient is lying on the stretcher.

The gurney 22 further includes a removable tarp 45 overlying the bottom surface 34 of the compartment 32 to facilitate the removal of the patient from the gurney. As illustrated, this tarp 45 includes handles 46 to facilitate lifting the patient from the compartment and transfer of the patient. The tarp 45 is disposable for health concerns.

The body suit 24 of the resuscitation apparatus effects cardio-pulmonary resuscitation and further externally cools the body of the patient. For this purpose, the body suit 24 has a thoracic cuff 26 and an abdominal cuff 28 releasably attachable through the use of Velcro fasteners 50 around the respective thoracic and abdominal region of the patient. Each of these cuffs includes an internal bladder in fluid communication with the coolant source (i.e., the $CO_2$ cartridge) and is sequentially inflatable and deflatable by the respective introduction and evacuation of the $CO_2$ in the bladder. Coolant fluid moves by expansion from the tank 43 to each respective cuff. The inflation of the abdominal cuff 28 causes compression of the abdominal region of the patient to force the exhalation of air in the lungs L. Deflating the abdominal cuff 28 permits inhalation in the lungs. Likewise, the sequential compression and release of the thoracic cuff 26 causes the external massaging of the heart to effect circulation of the blood.

The resuscitation apparatus further uses sequential external counterpulsation technology to facilitate blood circulation. For this, the body suit 24 includes lower-torso cuffs. The lower-torso cuffs (not shown) include a pair of leg cuffs and a buttock cuff. These cuffs work like a pulsating blood-pressure cuff to force blood from the legs and thighs back to the heart in a powerful wave-like flow. The cuffs are sequentially inflated such that pressure is exerted initially on the lower leg, moving to the upper thigh and finally the buttocks to drive more blood back to the heart. The lower torso cuffs are controlled by a electronic control console, a pneumatic control console, and an air compressor. These components are carried on the gurney 22 of the present invention.

The head cooling device 30 of the apparatus is designed to effect extracranial cooling of the brain and internal cooling of both the sinus cavities and core of the body. For this purpose, the head-cooling device 30 includes a helmet 52 adapted to be mounted on the head of the patient. This helmet 52 has an outer shell 54 and a bladder 56 mounted on at least a portion of the inner surface thereof and preferably, the entire inner surface of the helmet. The bladder 56 is in fluid communication with the coolant source so that the coolant source can be infused into the bladder until a tight fit over the head of the patient is achieved. The bladder 56 is detachable from the inner surface of the outer shell 54 for sanitary disposal of the bladder.

The helmet 52 further cools the lungs and the blood of the patient. For this purpose, the helmet includes a mask 58 having a fitting that covers the patient's mouth and nose. As is typical for respirators, the fitting is in fluid communication with a source of oxygen 59, which travels through the nose of the patient into the patient's lungs L. The source of oxygen 59 is preferably cooled so that as it travels through the sinuses of the patient, the cooled oxygen cools the sinus cavities and, indirectly, the brain of the patient. In the lungs, the cooled oxygen cools the core of the patient's body and the blood of the patient.

The mask 58 further includes a nasogastric tube 60 generally indicated at 60 to further facilitate the quick cooling of the patient. This tube extends through the fitting and nose of the patient to the stomach S. The nasogastric tube 60 preferably includes a first passageway 62 and a second passageway 64. The first passageway 62 of the tube is in fluid communication with a source of cooled saline 63 and is adapted to infuse the cooled saline into the stomach to cool the body of the patient. The second passageway 64 is connected to a vacuum 66 for evacuating the saline 63 from the stomach. Preferably, an inflatable balloon 70 is affixed to the nasogastric tube 60 to prevent the nasogastric tube from being pulled out of the stomach S unintentionally. The balloon 70 is located on the nasogastric tube 60 to engage the upper, interior surface 72 of the stomach adjacent the esophagus. The nasogastric tube 60 extends downwardly from the balloon 70 a sufficient distance to insure that the second passageway 64 can evacuate the saline 63.

The apparatus 20 further includes a flexible neck cooling device 76 which surrounds the neck of the patient for cooling the neck. The neck cooling device 76 includes an internal bladder 78 in fluid communication with the $CO_2$ and is inflatable by infusion of the coolant to securely surround the neck and cool the neck. Alternatively, the neck cooling device 76 may be filled with materials which chill upon activation. For example, the neck cooling device 76 may be pre-filled with Ammonium Nitrate which reacts endothermically when activated by water to chill this device.

The resuscitation apparatus 20 further includes a diaphragm stimulator 80 to induce a cough-like response in the patient thereby effecting blood circulation. The diaphragm stimulator 80 comprises the means to stimulate the diaphragm. It includes an electric wire 82 connected to a source of electricity, the wire extending from the source of electricity to the diaphragm D of the patient where it terminates in a diaphragmatic band 84. The wire is preferably mounted on the nasogastric tube 60 and follows the tube through the sinuses of the patient into the esophagus E and to the diaphragm D where it terminates in the diaphragmatic band 84, which preferably surrounds the nasogastric tube 60. The source of electricity is adapted to selectively produce an electrical signal that the wire transmits to the diaphragmatic band 84 for stimulating the diaphragm. This electric shock in combination with the inhalation and quick expiration of air induced by the abdominal cuff 28 of the body suit 24 causes a cough-like response in the patient to effect blood circulation. Alternatively, the means to stimulate the diaphragm includes a transcutaneous stimulation. For this, an electrode patch (not shown) is placed on the skin and upon activation, transcutaneously stimulates the diaphragm to produce the same cough-like response in the patient.

The resuscitation apparatus 20 is controlled by a remote timing device 94. This timing device 94 controls the sequencing of the abdominal 28 and thoracic cuff 26 by causing the inflation and evacuation of each cuff. Thus, the timing device 94 controls the inhalation and quick exhalation of the lungs and the external massaging of the heart. Further, the timing device 94 controls the electric signal to the diaphragm 92. Thus, this timing device 94 can be arranged to stimulate the diaphragm 92 immediately following the quick exhalation of air from the lungs L. This combination induces the cough-like response in the patient to effect blood circulation.

In operation, the resuscitation apparatus 20 is rushed to an emergency site for a patient undergoing a cardiac arrest. The apparatus is equipped with cooled $CO_2$, cooled oxygen and cooled saline. The patient is placed in the refrigerated compartment 32 and the components of the apparatus (i.e., the body suit 24 and head cooling device 30) are installed on the patient to quickly induce hypothermia and to effect cardio-pulmonary resuscitation. The apparatus is installed by strapping the head cooling apparatus 30 and neck cooling apparatus 76 on the patient's head and connecting these components to the source of cooled $CO_2$ 43. The coolant is infused into the head 30 and neck 76 cooling apparatus so that they tightly fit around the patient's head and neck, respectively. Then, the mask 58 connected to the cooled oxygen 59 is placed over the patient's mouth and nose and the cooled oxygen is infused into the patient's sinuses and lungs. The nasogastric tube 60 connected to the cooled saline 63 is guided through the patient's nose into the stomach 72. The cooled saline 63 is infused through the tube into the stomach. At the same time, the abdominal 28 and thoracic cuffs 26 are strapped around the abdominal and thoracic region of the patient and the lower torso cuffs are strapped on the legs of the patient. The Velcro fasteners 50 of the abdominal and thoracic cuffs are connected and these cuffs inflated with the cooled $CO_2$. The lower cuffs are sequentially inflated by the air compressor and controlled by the electric and pnuemater control consoles.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. An apparatus for inducing hypothermia in a patient, the apparatus comprising:
    a coolant source adapted for absorbing heat in sufficient quantity and at a sufficient rate to quickly induce hypothermia,
    an oxygen source,
    a stretcher for supporting the patient, the stretcher having at least a portion thereof in fluid communication with the coolant source, and
    a head cooling device including a mask in fluid communication with the oxygen source for supplying oxygen to the lungs of the patient and a helmet adapted to be mounted on the head of the patient, the helmet being in fluid communication with the coolant source for extracranial cooling of the brain, the source of oxygen being cooled for supplying cooled oxygen to the lungs of the patient,
    the stretcher, coolant source, oxygen source and head cooling device being constructed and arranged for manually transporting the patient to a medical facility from a remotely located trauma site.

2. An apparatus as set forth in claim 1 further including a source of cooled saline and wherein the mask includes a nasogastric tube for infusing said cooled saline to the stomach to cool the body of the patient.

3. An apparatus as set forth in claim 2 wherein said nasogastric tube includes a first passageway for infusing said source of cooled saline into the stomach of the patient and a second passageway for evacuating the saline from the stomach.

4. An apparatus as set forth in claim 3 further including a diaphragm stimulator for inducing a cough-like response in the patient for effecting blood circulation, the stimulator being mounted on the nasogastric tube.

5. An apparatus as set forth in claim 2 further including means for stimulating the diaphragm to induce a cough-like response in the patient to effect blood circulation.

6. An apparatus as set forth in claim 5 wherein the diaphragm stimulating means comprises a source of electricity for selectively producing an electrical signal, a wire for transmitting the signal, and a diaphragmatic band for stimulating the diaphragm with the electric signal.

7. An apparatus as set forth in claim 6 wherein the wire for transmitting the electric signal is mounted on the nasogastric tube and the diaphragmatic band surrounds the nasogastric tube.

8. An apparatus as set forth in claim 1 wherein said coolant source comprises a compressed fluid capable of substantially decreasing in temperature upon decompression to a temperature sufficient to induce hypothermia in the patient.

9. An apparatus as set forth in claim 1 wherein the stretcher is a gurney, said gurney having legs capable of being collapsed for facilitating transport of the patient.

10. An apparatus as set forth in claim 9 wherein the gurney includes a removable tarp to facilitate removal of the patient from the gurney.

11. An apparatus as set forth in claim 1 wherein the stretcher includes a bottom having a compartment for storage of the source of coolant.

12. An apparatus as set forth in claim 11 wherein the bottom further includes at least one vent for the circulation of the coolant source over the patient as the patient is lying on the stretcher.

13. An apparatus as set forth in claim 1 wherein the bladder is removably mounted on the outer shell of the helmet.

14. An apparatus for inducing hypothermia and effecting blood circulation in a patient, the apparatus comprises,
    a stretcher having a refrigerated bottom for supporting and cooling the patient, and
    a body suit having a thoracic cuff and an abdominal cuff, said thoracic and said abdominal cuffs being sequentially inflatable and deflatable for sequentially compressing and releasing the thoracic and abdominal region of the patient thereby inducing inhalation and exhalation in the lungs and the circulation of the blood supply in the patient.

15. An apparatus as set forth in claim 14 further comprising means for sequentially inflating and deflating the thoracic and abdominal cuffs for sequentially compressing and releasing the thoracic and abdominal region of the patient.

16. An apparatus as set forth in claim 14 wherein the stretcher is a gurney, said gurney having legs capable of being collapsed for facilitating transportation of the patient.

17. An apparatus as set forth in claim 16 wherein the gurney includes a removable tarp to facilitate removal of the patient from the gurney.

18. An apparatus as set forth in claim 14 wherein the refrigerated bottom of the stretcher includes a compartment for storage of a source of coolant.

19. An apparatus for inducing hypothermia in a patient, the apparatus comprising:
    a coolant source adapted for absorbing heat in sufficient quantity and at a sufficient rate to quickly induce hypothermia,
    an oxygen source,
    a stretcher for supporting the patient, the stretcher having at least a portion thereof in fluid communication with the coolant source, and
    a mask in fluid communication with the oxygen source for supplying oxygen to the lungs of the patient, the source of oxygen being cooled for supplying cooled oxygen to the lungs of the patient,
    the stretcher, coolant source, oxygen source and mask being constructed and arranged for manually transporting the patient to a medical facility from a remotely located trauma site.

20. An apparatus for inducing hypothermia in a patient and effecting cardio-pulmonary resuscitation on the patient. the apparatus comprising.

a coolant source.

a cooled oxygen source.

a gurney for supporting and facilitating transport of the patient, the gurney having at least a portion thereof in fluid communication with the coolant source, a body suit having a thoracic cuff and an abdominal cuff, said thoracic and said abdominal cuffs being sequentially inflatable and deflatable for sequentially compressing and releasing the thoracic and abdominal region of the patient thereby inducing inhalation and exhalation in the lungs and the circulation of the blood supply in the patient, and a head cooling device including a helmet adapted to be mounted on the head of the patient, the helmet comprising an outer shell and a bladder mounted on the outer shell in fluid communication with the coolant source for extracranial cooling of the brain, and a mask in fluid communication with the oxygen source for supplying cooled oxygen to the lungs of the patient.

21. An apparatus as set forth in claim 20 further including a source of cooled saline and wherein the mask includes a nasogastric tube for infusing said cooled saline to the stomach to cool the body of the patient.

22. An apparatus as set forth in claim 21 wherein said nasogastric tube includes a first passageway for infusing said source of cooled saline into the stomach of the patient and a second passageway for evacuating the saline from the stomach.

23. An apparatus as set forth in claim 22 further including a diaphragm stimulator for inducing a cough-like response in the patient for effecting blood circulation, the stimulator being mounted on the nasogastric tube.

24. An apparatus as set forth in claim 20 wherein the thoracic cuff and abdominal cuff are in fluid communication with the coolant source, and wherein compression of said thoracic and said abdominal cuffs is effected by infusing said coolant source in said thoracic and said abdominal cuffs thereby cooling the body of the patient.

25. An apparatus for inducing hypothermia in a patient, the apparatus comprising:

a coolant source, an oxygen source, a stretcher for supporting the patient, the stretcher having at least a portion thereof in fluid communication with the coolant source, a head cooling device including a mask in fluid communication with the oxygen source for supplying oxygen to the lungs of the patient and a helmet adapted to be mounted on the head of the patient, the helmet comprising an outer shell and a bladder mounted on the outer shell in fluid communication with the coolant source for extracranial cooling of the brain, a source of cooled saline, the mask having a nasogastric tube for infusing the cooled saline to the stomach to cool the body of the patient, said nasogastric tube including a first passageway for infusing said source of cooled saline into the stomach of the patient and a second passageway for evacuating the saline from the stomach, and a diaphragm stimulator for inducing a cough-like response in the patient for effecting blood circulation, the stimulator being mounted on the nasogastric tube.

26. An apparatus as set forth in claim 25 further comprising means for stimulating the diaphragm to induce a cough-like response in the patient to effect blood circulation.

27. An apparatus as set forth in claim 26 wherein the diaphragm stimulating means comprises a source of electricity for selectively producing an electrical signal, a wire for transmitting the signal, and a diaphragmatic band for stimulating the diaphragm with the electric signal.

28. An apparatus as set forth in claim 27 wherein the wire for transmitting the electric signal is mounted on the nasogastric tube and the diaphragmatic band surrounds the nasogastric tube.

29. An apparatus for inducing hypothermia in a patient, the apparatus comprising:

a coolant source, an oxygen source, a stretcher for supporting the patient, the stretcher having at least a portion thereof in fluid communication with the coolant source, a head cooling device including a mask in fluid communication with the oxygen source for supplying oxygen to the lungs of the patient and a helmet adapted to be mounted on the head of the patient, the helmet comprising an outer shell and a bladder mounted on the outer shell in fluid communication with the coolant source for extracranial cooling of the brain, the oxygen source being cooled for supplying cooled oxygen to the lungs of the patient.

30. An apparatus for inducing hypothermia in a patient, the apparatus comprising:

a coolant source, an oxygen source, a stretcher for supporting the patient, the stretcher having at least a portion thereof in fluid communication with the coolant source, the stretcher including a bottom having a compartment for storage of the source of coolant and at least one vent for the circulation of the coolant source over the patient as the patient is lying on the stretcher, and a head cooling device including a mask in fluid communication with the oxygen source for supplying oxygen to the lungs of the patient and a helmet adapted to be mounted on the head of the patient, the helmet comprising an outer shell and a bladder mounted on the outer shell in fluid communication with the coolant source for extracranial cooling of the brain.

31. An apparatus for inducing hypothermia and effecting blood circulation in a patient, the apparatus comprising:

a stretcher having a refrigerated bottom for supporting and cooling the patient, and a body suit having a thoracic cuff and an abdominal cuff, said thoracic and said abdominal cuffs being sequentially inflatable and deflatable for sequentially compressing and releasing the thoracic and abdominal region of the patient thereby inducing inhalation and exhalation in the lungs and the circulation of the blood supply in the patient, the thoracic cuff and abdominal cuff being in fluid communication with a coolant source, compression of the thoracic and abdominal cuffs being effected by infusing coolant from the coolant source in said thoracic and said abdominal cuffs thereby cooling the body of the patient.

32. An apparatus for inducing hypothermia and effecting blood circulation in a patient, the apparatus comprising:

a stretcher having a refrigerated bottom for supporting and cooling the patient, the refrigerated bottom of the stretcher including a compartment for storage of a source of coolant and at least one vent for the circulation of coolant from the coolant source over the patient as the patient is ling on the stretcher, and a body suit having a thoracic cuff and an abdominal cuff, said thoracic and said abdominal cuffs being sequentially inflatable and deflatable for sequentially compressing and releasing the thoracic and abdominal region of the patient thereby inducing inhalation and exhalation in the lungs and the circulation of the blood supply in the patient.

33. An apparatus as set forth in claim 32 further comprising means for sequentially inflating and deflating the thoracic and abdominal cuffs for sequentially compressing and releasing the thoracic and abdominal region of the patient.

34. An apparatus for inducing hypothermia in a patient, the apparatus comprising:

a coolant source adapted for absorbing heat in sufficient quantity and at a sufficient rate to quickly induce hypothermia, an oxygen source, a stretcher for supporting the patient, the stretcher having at least a portion thereof in fluid communication with the coolant source, and a mask in fluid communication with the oxygen source for supplying oxygen to the lungs of the patient, the stretcher, coolant source, oxygen source and mask being constructed and arranged for manually transporting the patient to a medical facility from a remotely located trauma site, said stretcher being a gurney having collapsible legs to facilitate transport of the patient, the legs being movable between an extended position in which the legs extend generally down from the gurney for supporting the gurney and a collapsed position in which the legs are collapsed beneath the gurney.

* * * * *